United States Patent [19]

Romano et al.

[11] 4,395,565

[45] Jul. 26, 1983

[54] PREPARING AROMATIC URETHANS

[75] Inventors: Ugo Romano, Vimercate; Giancarlo Fornasari, Milan; Sandro Di Gioacchino, Rome, all of Italy

[73] Assignee: Anic S.p.A., Palermo, Italy

[21] Appl. No.: 339,465

[22] Filed: Jan. 15, 1982

[30] Foreign Application Priority Data

Jan. 28, 1981 [IT] Italy ................. 19368 A/81

[51] Int. Cl.$^3$ ............................. C07C 125/065
[52] U.S. Cl. ........................ 560/24; 560/20; 560/27; 560/28; 560/29; 560/30; 560/32; 560/33
[58] Field of Search ............. 560/24, 157, 20, 27, 560/28, 29, 30, 32, 33

[56] References Cited

U.S. PATENT DOCUMENTS 4,268,684  5/1981  Gurgiolo ................. 560/24

OTHER PUBLICATIONS

The Merck Index, 7th Ed. (1960) p. 1114.

Primary Examiner—Bernard Helfin
Attorney, Agent, or Firm—Morgan, Finnegan, Pine, Foley & Lee

[57] ABSTRACT

A process for the preparation of aromatic urethans by reaction between aromatic amines and alkyl carbonates, said reaction being carried out in the presence of a catalyst composed of an alcoholate of an alkali metal or an alkaline earth metal. The reaction is caused to take place at a temperature which is variable from +50° C. and +150° C., in the liquid phase and with a molar ratio of the carbonate to the amine of from 10:1 to 1:10.

9 Claims, No Drawings

PREPARING AROMATIC URETHANS

This invention relates to a process for the preparation of aromatic urethans by the reaction between aromatic amines and alkyl carbonates, in the presence of a catalyst.

Urethans are commercially produced by reaction between an aromatic isocyanate and an hydroxyl-containing compound, the latter being usually an alcohol, and find their use as active ingredients in the formulation of pesticides.

It has been proposed, recently, to synthesize these compounds by reacting aromatic nitro-compounds, alcohols and carbon monoxide in the presence of selenium compounds (Italian Patent Specification No. 990 429).

The high price of selenium, the considerable toxicity of a few selenium compounds ($H_2Se$, SeCO) which are formed during progress of the reaction, the difficulties in totally recovering selenium from the reaction medium, the possibility that a certain amount of organic compounds of selenium be left in the end product, make such a technology difficult to be applied on a commercial scale.

It has now been found that aromatic urethans can be prepared by reacting alkyl carbonates with aromatic amines, basic catalysts being present.

The reaction in point takes place according to the following pattern:

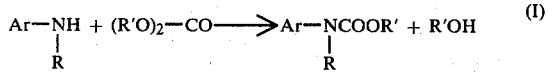

(I)

wherein Ar is an aromatic radical, R is hydrogen, an alkyl or an aralkyl radical, and R' is an alkyl or an aralkyl radical.

The aromatic amines which can be used in the process in question comprise the primary aromatic mono-amines, such as aniline and naphthylamine, the secondary aromatic monoamines having alkyl or aromatic substituents on the nitrogen atom, such as N-methyl, N-ethyl, N-propyl, benzyl aniline or diphenylamine, the aromatic monoamines which are substituted also in the ring nucleus with one or more radicals of the class of the alkyls, phenyls, alkoxy, phenoxy, chlorine, bromine, dialkylamino, nitro, such as toluidines, aminobiphenils, p-methoxy aniline, aminobiphenyl ethers, 4-methyl-3-chloro aniline, 4-chloro aniline, 3,4-dichloro aniline, bromo-aniline, metanitro-aniline, primary aromatic di-amines such as tolyl diamine, bis-phenylamino methane.

The carbonates which can be used in the process in question comprise those included in the class of the organic esters of the carbonic acid wherein the radicals are alkyls or aralkyls, both saturated or unsaturated, such as methyl, ethyl, nor.propyl, isopropyl, nor.butyl, isobutyl, sec.butyl, benzyl, phenylethyl, alkoxyethyl, phenoxyethyl, allyl. Particular advantages are achieved whenever the radicals which are present in the ester contain more than one carbon atom. Such substituents, as present in the carbonate molecule, can be either equal to or different from each other. The catalysts which can be recommended belong to the class of the alcoholates derived from alkali metals or alkaline earth metals, which preferably carry the same alkyls which are present in the molecule of the carbonate which is used on each particular occasion, such as lithium, sodium, potassium, magnesium, calcium methylate, ethylate, propylate and the like.

The reaction is caused to occur under appropriate temperature conditions (from $+50°$ C. to $+150°$ C.), but it is preferred to operate between $+100°$ C. and $+140°$ C., under such a pressure as is sufficient to maintain the reaction environment in the liquid phase, with molar ratios of the carbonate to the amine of from 10:1 to 1:10, but stoichiometric ratios are preferred, or an excess of the carbonate, one of the catalysts suggested above being present, in a molar ratio relative to the amine which is variable from 1:1 to 1:100, and preferably from 1:5 to 1:20.

On completion of the reaction, the catalyst can be separated from the medium (by settling or filtration) and recycled for a certain number of time to the reaction without any considerable loss of its activity.

When operating under the conditions suggested hereinbefore, the reaction displays very high selectivities relative to the carbamylate, inasmuch as the by-products which are formed are confined within a very narrow range.

EXAMPLE 1

A two-necked 100-ml flask, equipped with a thermometer and a magnetic stirrer, is charged with 1.24 g (0.024 mol) of sodium methylate, 18.5 g (0.199 mol) of aniline, 22 g (0.244 mol) of dimethyl carbonate and 25 mls of methanol, all these ingredients being charged in an anhydrous environment and under a nitrogen blanket.

The flask is placed in a thermostatically controlled oil bath so as to maintain the constancy of the temperature within the flask at 70° C. The reaction is continued under these conditions, with a continuous stirring, for 5 hours.

On completion of the reaction time, the flask is removed from the bath and, after having cooled the reaction mixture on ice, 18%-HCl is added in increments until the pH of the solution is nearly neutral (about 4 mls of acid are necessary).

A solid (NaCl) is separated, which is collected on a filter. The solution contains: methanol, dimethylcarbonate, aniline, N-methyl aniline and methyl carbanylate.

The conversion of aniline is 15.3% molar.

The selectivity relative to aniline, intended as the ratio of the mols of the product to the mols of converted aniline is: 98.8% for the carbanylate, and 1.2% for N-methylaniline.

EXAMPLE 2

A stainless-steel 150-ml autoclave is charged with 18.5 g (0.199 mol) of aniline, 21.8 g (0.242 mol) of the dimethylcarbonate, 1.33 g (0.024 mol) of sodium methylate. The autoclave is now immersed in an oil bath held at 120° C. for 5 hours. On completion, the autoclave is removed from the bath, allowed to cool and 50 g of ice are added, with 18%-HCl until neutralization occurs (about 4 mls of acid are required). Once the organic layer has been separated, the aqueous layer is extracted four times with 20 mls ethyl ether each time. The organic phase and the ethereal extract contain, all together: aniline, N-methyl aniline, N-methyl-methylcarbanylate, methylcarbanylate, methanol, dimethylcarbonate, biphenylurea. The molar conversion of aniline is 40%, the molar percent selectivity of the products which have been obtained, relative to aniline, is: 4.7% for methyl aniline, 16.5% for N-methyl-methylcarbanylate, 77.8% for methylcarbanylate and 1% for biphenylurea.

EXAMPLE 3

The reaction is carried out as is EXAMPLE 1, but at a temperature of +106° C.

There are charged 1.33 g (0.024 mol) of sodium methylate, 18.3 g (0.196 mol) of aniline, 29.0 g (0.24 mol) of diethyl carbonate. Upon cooling, there are added 50 g of ice and 18%-HCl to neutralization (about 4 mls of acid are necessary).

The aqueous layer is extracted four times with 20 mls ethyl ether each time and the extracts are combined with the oil which has been separated.

The analysis discloses the presence of methanol, ethanol, diethylcarbonate, aniline, methylcarbanylate, ethylcarbanylate, biphenylurea.

The conversion of aniline has been 34.6% and the selectivities in moles, are: 94.0% to ethylcarbanylate and 4.5% for methylcarbanylate and 0.7% for N-ethyl carbanylate and 0.8% of biphenylurea.

EXAMPLE 4

A stainless steel 150-ml autoclave is charged with 18.5 g (0.199 mol) of aniline, 28.5 g (0.242 mol) of diethyl carbonate, and 0.024 mol of sodium ethylate, all these ingredients being introduced with stirring at 120° C. for 5 hours. The next procedure is just as in EXAMPLE 3.

The analysis discloses the presence of ethanol, diethyl carbonate, aniline, ethylcarbanylate and N-ethylethylcarbanylate.

The conversion of aniline is 65.5% and the selectivities are: 95.2% for ethylcarbanylate, 2.5% for biphenylurea and 2.3% for N-ethyl-ethylcarbanylate.

EXAMPLE 5

Under the same conditions as in EXAMPLE 4, there are charged 18.8 g (0.202 mol) of aniline, 33.6 g (0.23 mol) of nor.propyl carbonate and 0.024 mol of sodium propylate and the mixture is allowed to react for 5 hours at +120° C.

In the reaction mixture, besides the unconverted reactants, there are: nor.propanol, propylcarbanylate and N-propyl-propylcarbanylate. The conversion of aniline is 61.3%. The selectivities are: 96% for propylcarbanylate, 1.5% for N-propyl-propylcarbanylate and 2.5% for biphenylurea.

EXAMPLE 6

In the apparatus described in EXAMPLE 4 there are charged 0.024 mol of sodium isopropylate, 33.6 g (0.230 mol) of diisopropyl carbonate and 18.8 g (0.202 mol) of aniline, the reaction being caused to take place for 5 hours at +120° C.

The reaction mixture is composed of diisopropylcarbonate, isopropanol, aniline, isopropylcarbanylate, biphenylurea, N-isopropyl-isopropylcarbanylate. The conversion of aniline is 46%. The respective selectivities are: 60.5% for isopropylcarbanylate, 0.3% for N-isopropyl-isopropylcarbanylate and 39.2% for biphenylurea.

EXAMPLE 7

The procedure is the same as for EXAMPLE 4, by charging 18.6 g (0.20 mol) of aniline, 41.7 g of dibutylcarbonate and 0.024 mol of sodium butylate, which are reacted for 5 hours at +120° C.

The conversion of aniline is 77.5%. The respective selectivities are: 98.4% for butylcarbanylate, 1.6% for N-butyl-butylcarbanylate.

EXAMPLE 8

There are charged, as in the previous Examples, 0.012 mol of sodium ethylate, 18.5 g (0.199 mol) of aniline and 28.6 g (0.24 mol) of diethylcarbonate. These reactants are reacted for 5 hours at +120° C.

The conversion of aniline is 54.4% and the respective selectivities are: 97.8% for ethylcarbanylate, 2.2% for N-ethyl-ethylcarbanylate.

EXAMPLE 9

There are charged, as usual, 0.024 mol of sodium ethylate, 57.2 g (0.48 mol) of diethylcarbonate and 18.6 g (0.20 mol) of aniline, and these are reacted for 5 hours at +120° C.

The conversion of aniline is 50% and the respective selectivities are: 97% for ethylcarbanylate and 3% for N-ethyl-ethylcarbanylate.

EXAMPLE 10

There are charged 0.024 mol of sodium ethylate, 28.6 g (0.24 mol) of diethylcarbonate and 18.6 g (0.20 mol) of aniline, all these being reacted at +135° C. for 5 hours. In the final ethereal solution there are contained: ethanol, diethylcarbonate, aniline, N-ethyl-ethylcarbanylate and ethylcarbanylate.

The conversion of aniline has been 81% and the respective selectivities were: 90.6% for ethylcarbanylate, 42% for N-ethyl-ethylcarbanylate and 5.2% for biphenylurea.

EXAMPLE 11

The test is performed as in EXAMPLE 4, by using a stainless steel 500-ml autoclave, charged with 92.5 g of aniline, 143 g of diethylcarbonate and 8.2 g of sodium ethylate.

On completion of the text, the aniline, upon addition of 200 mls of ether, was extracted from the organic layer by washing with water made acidic with HCl (60 mls at 18%).

From the organic layer there were obtained 2.3 g of biphenylurea, 100.4 g of ethylcarbanylate, 2.5 g of N-ethyl-ethylcarbanylate.

From the aqueous layer, upon neutralization with NaOH and extraction with ether there were recovered 31.4 g of aniline (unconverted).

EXAMPLE 12

The test is carried out as in EXAMPLE 4.

There are charged 0.024 mol of sodium ethylate, 144.4 g (0.969 mol) of diethylcarbonate and 18.6 g (0.20 mol) of aniline.

The conversion of aniline has been 87.3% and the respective selectivities are: 95.3% for ethylcarbanylate, 4.7% for N-ethyl-ethylcarbanylate.

EXAMPLE 13

The reaction of EXAMPLE 9 is repeated.

On completion of the reaction, the mixture is allowed to cool and filtered, the precipitate being washed with ethyl ether.

The solid matter, which is the catalyst, is recycled for a subsequent reaction, which is carried out under the same conditions.

In the recycle test for the catalyst, the results were a conversion of aniline of 47%, with a selectivity to ethylcarbanylate as high as 97.5%.

We claim:

1. A process for the preparation of aromatic urethans comprising the step of reacting, at a temperature between about 50° C. and about 150° C., an aromatic amine with an alkyl carbonate in the presence of a catalyst selected from among the alcholates of alkali metals or alkaline earth metals.

2. A process as defined in claim 1 wherein the reaction is carried out in a liquid phase.

3. A process as defined in claim 1 wherein the molar ratio of the carbonate to the amine is between about 10:1 and about 1:10.

4. A process as defined in claim 2 wherein the molar ratio of the carbonate to the amine is between about 10:1 and about 1:10.

5. A process as defined in claim 1 wherein the molar ratio of the catalyst to the amine is between about 1:1 and about 1:100.

6. A process as defined in claim 4 wherein the molar ratio of the catalyst to the amine is between about 1:1 and about 1:100.

7. A process as defined in claim 6 wherein the molar ratio of the catalyst to the amine is between about 1:5 and 1:20.

8. A process as defined in claim 1 wherein the reaction is carried out at a temperature between about 100° C. and about 140° C.

9. A process as defined in claim 1 wherein the reaction is carried out with an alkyl carbonate wherein at least one of the radicals contains more than one carbon atom.

* * * * *